United States Patent
Plunkett

(10) Patent No.: US 8,936,028 B2
(45) Date of Patent: Jan. 20, 2015

(54) LASER IMMUNOTHERAPY

(76) Inventor: Malcolm Plunkett, Adelaide (AU)

(*) Notice: Subject to any disclaimer, the term of this patent is extended or adjusted under 35 U.S.C. 154(b) by 79 days.

(21) Appl. No.: 13/636,359

(22) PCT Filed: Mar. 22, 2011

(86) PCT No.: PCT/AU2011/000321
§ 371 (c)(1),
(2), (4) Date: Feb. 22, 2013

(87) PCT Pub. No.: WO2011/116413
PCT Pub. Date: Sep. 29, 2011

(65) Prior Publication Data
US 2013/0144363 A1 Jun. 6, 2013

(30) Foreign Application Priority Data
Mar. 22, 2010 (AU) ................. 2010901213

(51) Int. Cl.
*A61B 19/00* (2006.01)
*A61N 5/06* (2006.01)
*A61F 9/008* (2006.01)
*A61N 5/067* (2006.01)

(52) U.S. Cl.
CPC .............. *A61N 5/0613* (2013.01); *A61F 9/008* (2013.01); *A61N 5/0624* (2013.01); *A61N 2005/067* (2013.01)
USPC ........................................... 128/898; 607/89

(58) Field of Classification Search
USPC ................... 607/88–94; 606/4–6; 128/898
See application file for complete search history.

(56) References Cited

U.S. PATENT DOCUMENTS 8,496,649 B2 * 7/2013 Previn et al. ................ 606/4
8,562,595 B2 * 10/2013 Plunkett et al. ............. 606/4
2005/0165385 A1 * 7/2005 Simon ......................... 606/4
2010/0049173 A1 * 2/2010 Plunkett et al. ............. 606/4
2010/0152716 A1 * 6/2010 Previn et al. ................ 606/4

FOREIGN PATENT DOCUMENTS

| WO | 2000/001444 | 1/2000 |
|---|---|---|
| WO | 2004/027487 | 4/2004 |
| WO | 2006/021040 | 3/2006 |
| WO | 2007/082047 | 7/2007 |
| WO | 2008/049164 | 5/2008 |
| WO | 2008/144828 | 12/2008 |

OTHER PUBLICATIONS

Williams et al. "Systemic immunostimmulation after retinal laser treatment in Retinis Pigmentosa." Clinical Immunology and Immunopathology. vol. 64(1):78-83, 1992.*
Komelkova, L.V., et al. "Biochemical and immunological indices of blood in Parkinson's disease and correction of these indices by means of laser therapy." Patol. Fizio. Eksper.Ter. 2004;1:15-18.
Williams, L.L., et al. "Systemic immunostimmulation after retinal laser treatment in Retinis Pigmentosa." Clinical Immunology and Immunopathology. 1992;64(1):78-83.

* cited by examiner

*Primary Examiner* — Ahmed Farah
(74) *Attorney, Agent, or Firm* — Kathleen D. Rigaut; Robert C. Netter, Jr.; Dann, Dorfman, Herrell & Skillman

(57) ABSTRACT

A method of immunotherapy of a mammal, or a laser device therefor, includes the step of treating one or more immune privileged cells, tissues or organs of said mammal with a laser to reduce or eliminate the immune privilege status of said one or more cells, tissues and/or organs to thereby elicit an immune response that is beneficial to the mammal. The method of immunotherapy avoids or minimizes lasting damage to the treated cells, tissues and/or organs. The laser treatment is typically, although not exclusively, to the pigmented epithelium of the eye or eyes. The method may be for treating a disease or condition selected from: a bacterial infection; a viral infection; early AMD; glaucoma; diabetic retinopathy; multiple sclerosis; Parkinson's disease; and Alzheimer's disease. Typically, the radiant exposure level of the laser treatment is no greater than 60-100% of a visible effect threshold.

11 Claims, 1 Drawing Sheet

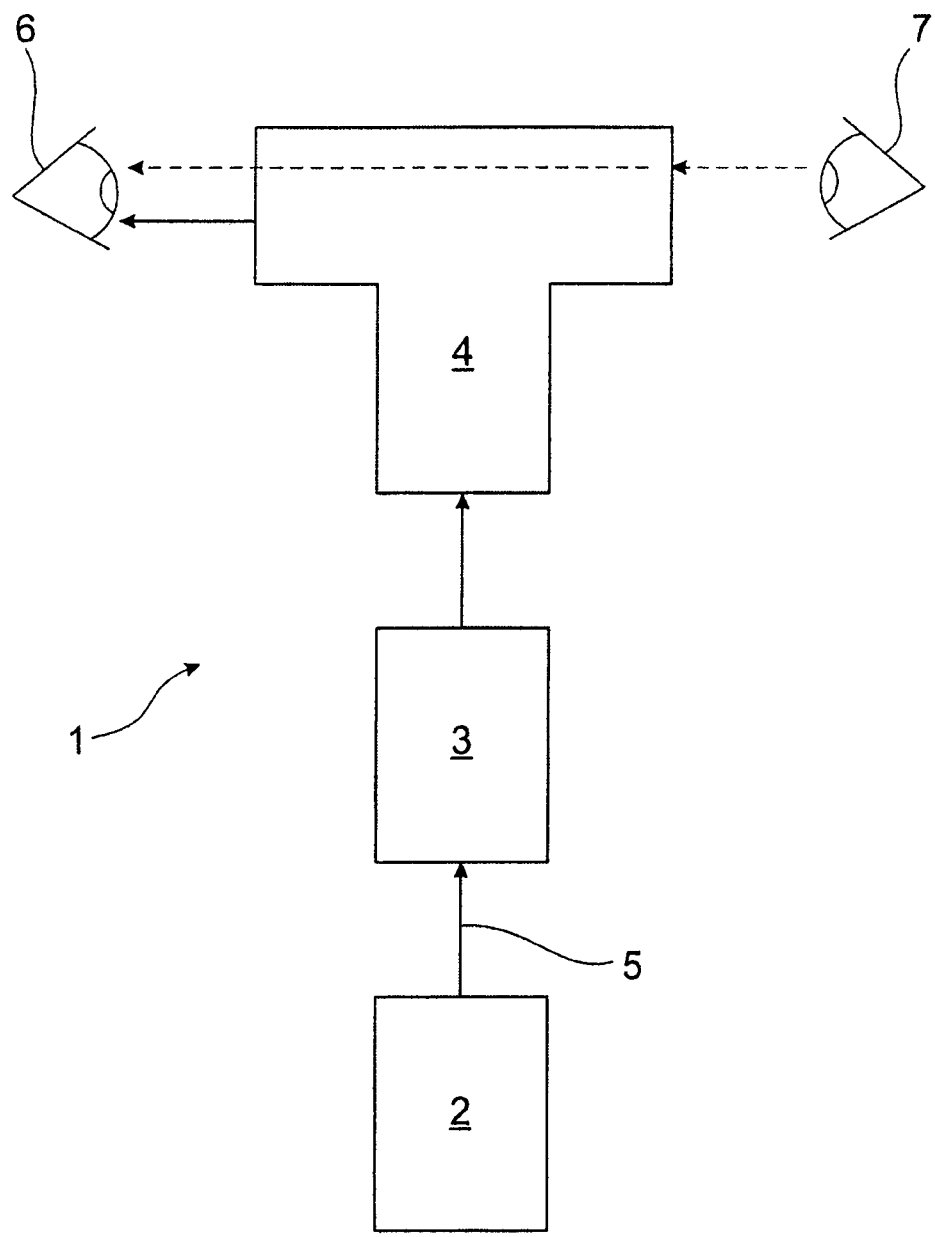

LASER IMMUNOTHERAPY

The present application is §371 application of PCT/AU2011/000321 filed Mar. 22, 2011 which claims priority to AU Patent Application No. 2010901213 filed Mar. 22, 2010, the entire disclosure of each being incorporated by reference herein.

FIELD OF THE INVENTION

This invention relates to a laser treatment of immune privileged cells tissues or organs such as the eye, brain or testis. More particularly, this invention relates to a laser treatment of dysfunction within immune privileged cells, tissues or organs which modifies immune privilege status to thereby enable the elicitation of a beneficial immune response.

BACKGROUND TO THE INVENTION

Immune privilege is an immunological phenomenon whereby some cells, tissues and organs fail to invoke a full immune response to foreign antigens, such as present in foreign cells, tissues, organs and pathogens. Traditionally, this phenomenon has had great impact on tissue transplantation. For example, foreign tissue grafts placed in immune privileged sites (e.g. anterior chamber of the eye, cornea, brain, testis, pregnant uterus) enjoy extended, often indefinite, survival, whereas similar grafts placed at sites that are not immune privileged (e.g. skin, kidney capsule) are rapidly rejected. Similarly, grafts prepared from immune privileged tissues experience extended, often indefinite, survival when implanted at body sites which normally reject foreign tissue.

Immune privilege is granted to the eye because the retina contains a complex matrix of tissue and cells, some of which are post-mitotic, which may be damaged if exposed to the full weight of the systemic immune and inflammatory responses. Immune privilege is maintained by the physical barrier of epithelial cells layers, and also by the active expression of immunosuppressive and anti-inflammatory factors by ocular cells.

This tradeoff between possible collateral damage and disease control is maintained except under extraordinary circumstances such as a serious physical injury or an infection which could potentially threaten the life of the host. Under these conditions the immune privilege status can be modified to allow to all or part of the systemic immune and inflammatory responses access into the eye. For example, it has been reported that retinal laser burn (RLB) not only causes damage to the eye but also causes a loss of immune privilege in both the burned and unburned eye (Qiao et al., 2009, Am. J. Pathol. 174 414).

OBJECT OF THE INVENTION

It is an object of this invention to provide a laser treatment and/or a laser device suitable for treatment of an immune privileged cell tissue or organ to thereby elicit a beneficial immune response.

A preferred object of the invention is that the method of immunotherapy and/or laser device avoid or minimize causing lasting damage to the treated cells, tissues and/or organs.

Further objects will be evident from the following description.

DISCLOSURE OF THE INVENTION

In one form, although it need not be the only or indeed the broadest form, the invention resides in a method of immunotherapy of a mammal in need of such treatment, said method including the step of treating one or more immune privileged cells, tissues or organs of said mammal with a laser to modify the immune privilege status of said one or more cells, tissues and/or organs to thereby elicit an immune response that is beneficial to the mammal.

In another form, the invention resides in a laser device for treating one or more immune privileged cells, tissues or organs of a mammal to modify the immune privilege status of said one or more cells, tissues and/or organs and thereby elicit an immune response that is beneficial to the mammal.

Suitably, the method of immunotherapy and/or laser device avoids or minimizes lasting damage to the treated cells, tissues and/or organs.

Preferably, the one or more immune privileged cells, tissues or organs include the eye, brain or testis. The laser treatment of the eye is preferably directed to the pigmented epithelium (PE) of one or both eyes.

Suitably, the method and/or laser device is for treating a disease or condition in the mammal selected from: a bacterial infection; a viral infection; Early age-related macular degeneration (AMD); glaucoma; diabetic retinopathy; multiple sclerosis; and a neurodegenerative condition. The neurodegenerative condition may be selected from Parkinson's disease and Alzheimer's disease. Preferably, the mammal is a human.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWING

To assist in understanding the invention preferred embodiments will now be described with reference to the following figures in which:

FIG. 1 is a block diagram of a laser device.

DETAILED DESCRIPTION

The invention described herein provides a method of immunotherapy by laser treatment of dysfunction within one or more immune privileged cells, tissues or organs to modify immune privilege. Furthermore, the method of treatment is essentially painless and avoids lasting collateral damage to the cells tissues or organs subjected to the laser treatment. Non-limiting examples of immune privileged cells, tissues and organs include the eye, brain, testis and placenta. According to the invention, some aspects of the privileged immune privilege system may be modified, or the immune privilege system may be modified at one or more particular physical locations, or the entire immune privilege system may be modified. Preferably, modifying the immune privilege status includes reducing or attenuating immune privilege status.

Although not wishing to be bound by theory, it is proposed that in diseases such as diabetes, glaucoma and AMD, a range of low-level para-inflammatory problems have been able to develop in the eye over time because immune privilege is active. In AMD the genes that greatly increase the likelihood of suffering from AMD are related to the immune and inflammatory response. Moreover, it is proposed that AMD is caused by chronic para-inflammatory and immune responses which were initiated by a brief, mild infection or injury, but have not since fully switched off (and are therefore "dysfunctional"), resulting in one or more disease pathologies developing over time. Similar immune dysfunction may also occur in other immune privileged organs such as brain or testis. The eyes are considered to be an extension of the brain and both share a common immune privileged status within the central nervous system.

The laser treatment of the invention suitably results in modifying the immune privilege status of the treated cells, tissues or organs in the mammal, for sufficient time to potentiate or allow the elicitation of an immune response beneficial to the mammal. The elicited response is beneficial to the mammal by allowing systemic immune and inflammatory responses to overcome inappropriate or dysfunctional inflammation, autoimmune or allergic responses that have developed under immune privilege. The beneficial immune response may be characterized by the elicitation of elements of either or both of the systemic adaptive and innate immune systems. These include the elicitation of immune responses mediated by one or more of $CD4^+$ and $CD8^+$ T cells, B cells, NK cells and myelomonocytic cells, although without limitation thereto. Such responses may include the production of antibodies, complement and/or immunomodulators such as interleukins, cytokines and chemotactic factors.

Preferably, the method of immunotherapy avoids lasting damage to the treated cells, tissues and/or organs. The laser causes a discrete focal insult (e.g. at the level of the PE in the eye) which results in virtually no collateral damage and no lasting damage at the treatment site.

It will be appreciated that the method of treatment may be practiced on any mammal, including humans, livestock and domestic pets. Preferably, the mammal is a human In embodiments where the immune privileged organ is the eye, treatment of the subject mammal is by applying laser energy from the laser to the pigmented epithelium (PE) of one or both eyes. The laser can be applied to the retinal pigmented epithelium (RPE), iris, trabecular meshwork, or any other part of the PE that is accessible to the laser, depending on the ocular disorder involved. Disease pathology that predominately affects the macula, such as Early AMD would preferably be given treatment by the laser device to the RPE nearby the macula but away from the fovea. Disease pathology that predominately affects the aqueous outflow area, such as glaucoma, would preferably be given treatment by the laser device to the trabecular meshwork.

In a clinical setting, the preferred method of potentiating an immune response in the eye includes the step of identifying ocular pathology which indicates, or is consistent with, para-inflammatory dysfunction.

In one example, early age-related macular degeneration (AMD), this pathology could include one or more of the following;
 (i) macular drusen
 (ii) macular pigmentation changes
 (iii) elevated levels of C-Reactive Protein (CRP) in blood plasma, or other biomarkers of ocular inflammation and/or
 (iv) degraded retinal function within the macula, as measured by dark-adapted recovery times from photostress, or other visual function tests.
In another example, Primary Open Angle Glaucoma (POAG), this pathology could include;
 (a) loss of peripheral visual fields and/or
 (b) elevated intra-ocular pressure A laser device suitable for performing the method of the invention delivers pulses of laser energy of relatively short duration and high peak power, and at a wavelength that is preferentially absorbed by the treated cells tissues or organs. Typical laser parameters would be a laser pulse or sequence of laser pulses each having:

(A) a pulse duration in the range of 50 ps to 500 ns,
(B) a wavelength in the range 500 nm to 900 nm; and
(C) a pulse energy in the range 10 μJ to 10 mJ.

In particular embodiments relating to the treatment of the eye, where delicate cellular structures reside above the pigmented epithelium, such as the retina above the retinal pigmented epithelium (RPE), a preferred laser device is described in International Publication WO2008144828 and briefly with reference to FIG. 1.

In FIG. 1 there is shown a block diagram of a laser device 1. The laser device 1 comprises a laser module 2 producing a laser pulse or sequence of laser pulses each having a pulse duration in the range of 50 ps to 500 ns, a wavelength in the range 500 nm to 900 nm and a pulse energy in the range 10 μJ to 10 mJ. The laser device 1 further comprises a uniform irradiance module 3 that modifies an output beam profile of the laser module to produce a uniform treatment effect, and a beam delivery and viewing module 4 that delivers the laser pulse or pulses to the retina with a radiant exposure in the range of 8 $mJ/cm^2$ to 8000 $mJ/cm^2$ per pulse. A laser beam 5 is generated by the laser module 2, manipulated for uniform irradiance by the uniform irradiance module 3 and directed to the eye 6 of a patient by the beam delivery and viewing module 4. The beam delivery and viewing module 4 incorporates a coincident viewing path for an operator 7.

In use the laser device 1 irradiates the pigmented epithelium (PE) of the eye to produce intracellular micro-bubbles within the PE cells. The laser is optimized to deliver laser energy in a manner that causes rapid heating of the surface of pigmented granules within the PE cells, producing intracellular gas bubbles, but without sufficient time for the heat produced to diffuse through the outer cell membrane, thereby avoiding collateral damage. This is achieved by using pulses of laser energy of relatively short duration and high peak power, and at a wavelength that is preferentially absorbed by the RPE. Typically, radiant exposure is in the range 20 $mJ/cm^2$ to 300 $mJ/cm^2$ per pulse. The pulse duration is around 3 ns. The wavelength is suitably about 532 nm.

The intracellular gas bubbles produced within the PE cells cause damage to the internal structure of the cells resulting in acute or delayed cell death. The expansion and collapse of the gas bubbles also produces acoustic shock waves which radiate in all directions away from the source. The result of these effects is that sensory nerve ends within the adjacent choroid are triggered into a response which modifies the immune privilege in the treated eye or both eyes, as part of a bilateral autonomic neural response.

As described in WO2008/049164, when 3 ns pulses are used the first visible effect is from the formation of a macro-bubble, which results from intra-cellular micro-bubbles bursting the RPE cell membranes and coalescing into a visible macro-bubble. Therefore, radiant exposure levels no greater than 60-100% of the visible effect threshold (VET) are preferred to reduce the risk of damaging overlying photoreceptors. Particular values may be 60%, 65%, 70%, 75%, 80%, 85%, 90%, 95% or 100% of the VET.

Accordingly, the treatment radiant exposure may be titrated to a particular percentage below the VET in order to set the optimum value for each individual treated.

The effect of this is treatment of the ocular immune system to modify its immune privileged status. While this treatment may result in the death of a small number of PE cells within the treatment area, these are quickly replaced by migrating and dividing PE cells which restore the physical epithelial barrier without any lasting damage.

As a result of the treatment, the systemic immune system may gain access to the eye to potentially respond to chronic dysfunctional para-inflammatory, degenerative or infectious conditions, which have developed under ocular immune privilege. Examples of this are Early AMD, glaucoma and diabetic retinopathy. It is also contemplated that an immune response may be elicited against pathogens such as viruses and bacteria which exploit the immune privileged status of the eye. Examples include pathogens which cause conjunctivitis, bletharitis, keratitis and endophthalmitis, although without limitation thereto. Particular bacterial pathogens may include *Staphylocccus* sp, *Proprionibacterium* sp, *Haemophilus* and *Streptococcus* sp, although without limitation thereto.

While the preferred embodiment of the method of treatment is described herein with reference to the eye, the method of treatment and laser device may also be also be used to treat other immune privileged tissues and organs. Non-limiting examples include brain and testis. With regard to treatment of the brain, the invention contemplates treatment of degenerative neurological disorders of the brain and central nervous system (CNS). Neurological disorders treatable according to the invention are suitably responsive to elimination of immune privilege. These include neuro-inflammatory conditions such as multiple sclerosis and neurodegenerative disorders such as Alzheimer's disease and Parkinson's disease.

As the eyes are extensions of the brain, within the CNS, brain and neurological disorders may be treated by laser application to the PE of the eye(s) in order to alter the immune privileged status of the CNS.

Alternatively, by gaining access to the ventricles of the brain via standard surgical techniques laser energy can be delivered to the choroid plexus via a specially designed optical fibre probe. The tip of the probe is coated with extremely small diameter (approx 5 micron) absorbing spheres or discs which absorb the laser energy and produce micro-bubbles and shock waves.

Using video observation the tip of the probe is placed on the choroid plexus and the laser pulse applied, so that shockwaves from the expansion and collapse of the bubbles causes death of a few choroid plexus epithelial cells via damage to their cytoskeleton, and cause acoustic shock waves, resulting in a lowering or modifying of immune privilege which allows the systemic immune and inflammatory processes to improve degradation caused by the chronic dysfunction para-inflammation, as described above.

Persons skilled in the field will be aware of specific optical elements that may be substituted for one or more of the elements described for the preferred embodiment without departing from the spirit and scope of the invention. Throughout the specification the aim has been to describe the invention without limiting the invention to any one particular combination of preferred features or embodiment.

All computer programs, algorithms, patent and scientific literature referred to herein is incorporated herein by reference.

The invention claimed is:

1. A method of immunotherapy of a neurodegenerative disease or condition in a mammal in need of such treatment, said method including the step of irradiating the pigmented epithelium (PE) of the eye or eyes of said mammal with a laser to reduce or eliminate the immune privilege status of one or more cells, tissues and/or organs of the central nervous system of said mammal, wherein a radiant exposure level of the laser treatment is no greater than 60-100% of a visible effect threshold (VET), to thereby elicit an immune response that is beneficial to the mammal and thereby treat said neurodegenerative disease or condition in the mammal.

2. The method of immunotherapy of claim 1, which avoids or minimizes lasting damage to the irradiated pigmented epithelium (PE) of the eye or eyes.

3. The method of claim 1, wherein the neurodegenerative condition is selected from Parkinson's disease and Alzheimer's disease.

4. The method of claim 1, wherein the mammal is a human.

5. The method of claim 1, wherein the radiant exposure level is 60%, 65%, 70%, 75%, 80%, 85%, 90%, 95%, or 100% of the VET.

6. The method of claim 1, wherein the immune response is characterized by the elicitation of elements of the adaptive and/or innate immune systems.

7. The method of claim 6, wherein the immune response includes the elicitation of one or more of CD4+ T cells, CD8+ T cells, B cells, antibodies, interleukins, cytokines, chemotactic factors, NK cells and/or myelomonocytic cells.

8. The method of claim 1, wherein the laser delivers a pulse or sequence of laser pulses each having:
 (A) a pulse duration in the range of 50 ps to 500 ns;
 (B) a wavelength in the range 500 nm to 900 nm; and
 (C) a pulse energy in the range 10 µJ to 10 mJ.

9. The method of claim 8, wherein the pulse wavelength is about 532 nm.

10. The method of claim 8, wherein the pulse duration is about 3 ns.

11. The method of claim 1, wherein radiant exposure is in the range 20 mJ/cm2 to 300 mJ/cm2 per pulse.

* * * * *